(12) United States Patent
Falci (10) Patent No.: US 9,452,226 B2
(45) Date of Patent: *Sep. 27, 2016

(54) RODENT MODEL OF CENTRAL NEUROPATHIC PAIN CAUSED BY DORSAL ROOT ENTRY ZONE AVULSION AT T13

(71) Applicant: Scott P. Falci, Morrison, CO (US)

(72) Inventor: Scott P. Falci, Morrison, CO (US)

(*) Notice: Subject to any disclaimer, the term of this patent is extended or adjusted under 35 U.S.C. 154(b) by 178 days.

This patent is subject to a terminal disclaimer.

(21) Appl. No.: 13/960,465

(22) Filed: Aug. 6, 2013

(65) Prior Publication Data

US 2014/0041065 A1    Feb. 6, 2014

Related U.S. Application Data

(63) Continuation of application No. 12/541,754, filed on Aug. 14, 2009, now Pat. No. 8,502,017.

(60) Provisional application No. 61/088,978, filed on Aug. 14, 2008.

(51) Int. Cl.
| | |
|---|---|
| *A01K 67/033* | (2006.01) |
| *A61K 49/00* | (2006.01) |
| *A01K 67/027* | (2006.01) |
| *G01N 33/50* | (2006.01) |
| *A61K 9/00* | (2006.01) |

(52) U.S. Cl.
CPC ......... *A61K 49/0008* (2013.01); *A01K 67/027* (2013.01); *G01N 33/5088* (2013.01); *A01K 2207/30* (2013.01); *A01K 2227/105* (2013.01); *A01K 2267/0393* (2013.01); *A61K 9/0085* (2013.01)

(58) Field of Classification Search
CPC .................. A01K 2207/30; A01K 2227/105; A61K 2227/105; A61K 49/0008; A61K 9/0085; G01N 33/5088
See application file for complete search history.

(56) References Cited

U.S. PATENT DOCUMENTS

| | | |
|---|---|---|
| 7,130,691 B2 | 10/2006 | Falci |
| 8,502,017 B2 * | 8/2013 | Falci ............................. 800/14 |
| 2004/0006376 A1 | 1/2004 | Falci |
| 2007/0016264 A1 | 1/2007 | Falci |
| 2011/0229412 A1 | 9/2011 | Falci |

FOREIGN PATENT DOCUMENTS

WO    2006122035 A2    11/2006

OTHER PUBLICATIONS

Abraham et al., "Spinal and supraspinal changes in opioid mRNA expression are related to the onset of pain behaviors following excitotoxic spinal cord injury," Pain 90, 2001a, 181-190.

Abraham, "The role of kainic acid/AMPA and metabotropic glutamate receptors in the regulation of opioid mRNA expression and the onset of pain-related behavior following excitotoxic spinal cord injury," Neuroscience 104, 2001b, 863-874.

Baastrup et al., "Pharmacological management of neuropathic pain following spinal cord injury," CNS Drugs 22, 2008, 455-475.

Basso et al., "A sensitive and reliable locomotor rating scale for open field testing in rats," J. Neurotrauma 12, 1995, 1-21.

Beniczky et al., "Evidence-based pharmacological treatment of neuropathic pain syndromes," J. Neural Transm. 112, 2005, 735-749.

Berman et al., "Pain following human brachial plexus injury with spinal cord root avulsion and the effect of surgery," Pain 75, 1998, 199-207.

Bigbee et al., "At-level neuropathic pain is induced by lumbosacral ventral root avulsion injury and ameliorated by room reimplantation into the spinal cord," Exp. Neurol. 204, 2007, 273-282.

Browder et al., "Do Sympathetic Nerves Transmit Painful Impulses?," The American Journal of Surgery 18, 1932, 100-102.

Carlstedt, "Root repair review: basic science background and clinical outcome," Restor. Neurol. Neurosci. 26, 2008, 225-241.

Chacur et al., "A new model of sciatic inflammatory neuritis (SIN): induction of unilateral and bilateral mechanical allodynia following acute unilateral peri-sciatic immune activation in rats," Pain 94, 2001, 231-244.

Chu et al., "Implantation of neurotrophic factor-treated sensory nerve graft enhances survival and axonal regeneration of motoneurons after spinal root avulsion," J. Neuropathol. Exp. Neurol. 68, 2009, 94-101.

Davies et al., "Astrocytes derived from glial-restricted precursors promote spinal cord repair," J. Biol. 5, 2006, 7.

Devivo, "Causes and costs of spinal cord injury in the United States," Spinal Cord 35, 1997, 809-813.

Echlin, "Pain Responses on Stimulation of the Lumbar Sympathetic Chain under Local Anesthesia," Journal of Neurosurgery, 1949, 530-533.

Edgar et al., "Computer-assisted DREZ microcoagulation: post-traumatic spinal deafferentation pain," J. Spinal Disord. 6, 1993, 48-56.

Falci et al., "Dorsal root entry zone microcoagulation for spinal cord injury-related central pain: operative intramedullary electrophysiological guidance and clinical outcome," J. Neurosurg. 97, 2002, 193-200.

Gorman, "Conditions affecting the onset, severity, and progression of a spontaneous pain-like behavior after excitotoxic spinal cord injury," J. Pain 2, 2001, 229-240.

Gwak et al., "Effect of age at time of spinal cord injury on behavioral outcomes in rat," J. Neurotrauma 21, 2004, 983-993.

Gwak et al., "Remote astrocytic and microglial activation modulates neuronal hyperexcitability and below-level neuropathic pain after spinal injury in rat," Neuroscience 161, 2009, 895-903.

Hains et al., "Serotonergic neural precursor cell grafts attenuate bilateral hyperexcitability of dorsal horn neurons after spinal hemisection in rat," Neuroscience 116, 2003, 1097-1110.

Hargreaves et al., "A new and sensitive method for measuring thermal nociception in cutaneous hyperalgesia," Pain 32, 1988, 77-88.

(Continued)

*Primary Examiner* — Deborah Crouch
(74) *Attorney, Agent, or Firm* — Polsinelli PC (57) ABSTRACT

The present disclosure describes an animal model of central neuropathic pain relevant to spinal cord injury, as well as methods of using the model to screen for therapeutic agents and to test existing therapies.

11 Claims, 7 Drawing Sheets

(56) References Cited

OTHER PUBLICATIONS

Harris, "The Role of the Sympathetic in Sensory Conduction and Certain Neuralgias," British Medical Journal 2, 1936, 112-115.
Harvey, "Efficient estimation of sensory thresholds," Behav. Res. Methods Inst. Comp. 18, 1986, 623-632.
Huang et al., "The mirror-image pain: an unclered phenomenon and its possible mechanism," Neurosci. Biobehav. 34, 2010, 528-532.
Hulsebosch et al., "Rodent model of chronic central pain after spinal cord contusion injury and effects of gabapentin," J. Neurotrauma 17, 2000, 1205-1217.
Jones et al., "Calcium-permeable alpha-amino-3-hydroxy-5-methyl-4-isoxazolepropionic acid/kainate receptors mediate development, but not maintenance, of secondary allodynia evoked by first-degree burn in the rat," J. Pharmacol. Exp. Ther. 310, 2004, 223-229.
Keown et al., "Methods for Introducing DNA into Mammalian Cells," Methods in Enzymology 185, 1990, 527-537.
Lampert et al., "Upregulation of persistent and ramp sodium current in dorsal horn neurons after spinal cord injury," Exp. Brain Res. 174, 2006, 660-666.
Lombard et al., "Deafferentation hypersensitivity in the rat after dorsal rhizotomy: a possible animal mode of chronic pain," Pain 6, 2, 1979, 163-174.
McEwen et al., "Quantification of locomotor recovery following spinal cord contusion in adult rats," J. Neurotrauma 23, 2006, 1632-1653.
McQuay et al., "A systematic review of antidepressants in neuropathic pain," Pain 68, 1996, 217-227.
McQuay et al., "Anticonvulsant drugs for management of pain: a systematic review," British Medical Journal 311, 1995, 1047-1052.
Milligan et al., "Intrathecal HIV-1 envelope glycoprotein gp120 induces enhanced pain states mediated by spinal cord proinflammatory cytokines," J. Neurosci. 21, 2001, 2808-2819.
Milligan et al., "Spinal glia and proinflammatory cytokines mediate mirror-image neuropathic pain in rats," J. Neurosci. 23, 2003, 1026-1040.
Milligan et al., "Thermal hyperalgesia and mechanical allodynia produced by intrathecal administration of the human immunodeficiency virus-1 (HIV-1) envelope glycoprotein, gp120," Brain Res. 861, 2000, 105-116.
Ovelmen-Levitt et al., "Dorsal root rhizotomy and avulsion in the cat: a comparison of long term effects on dorsal horn neuronal activity," Neurosurgery 15, 1984, 921-927.
Penas et al., "Cytoskeletal and activity-related changes in spinal motoneurons after root avulsion," J. Neurotrauma 26, 2009, 763-779.
Rodrigues Hell et al., "Local injection of BDNF producing mesenchymal stem cells increases neuronal survival and synaptic stability following ventral root avulsion," Neurobiol. Dis. 33, 2009, 290-300.
Scorisa et al., "Glatiramer acetate positively influences spinal motoneuron survival and synaptic plasticity after ventral root avulsion," Neurosci. Lett. 451, 2009, 34-39.
Shields, "Functional Anatomy of the Autonomic Nervous System," Jounal of Clinical Neurophysiology 10, 1993, 2-13.
Siddall et al., "A longitudinal study of the prevalence and characteristics of pain in the first 5 years following spinal cord injury," Pain 103, 2003, 249-257.
Siddall et al., "Management of neuropathic pain following spinal cord injury: now and in the future," Spinal Cord 47, 2009, 352-359.
Siddall et al., "Pain following spinal cord injury, in: Handbook of Clinical Neurology," F. Cervero and T.S. Jensen (eds), Elsevier: Philadelphia, 2006, 689-703.
Sorkin et al., "Antibody directed against GD(2) produces mechanical allodynia, but not thermal hyperalgesia when administered systematically or intrathecally despite its dependence on capsaicin sensitive afferents," Brain Res. 930, 2002, 67-74.
Spataro et al., "Spinal gap junctions: potential involvement in pain facilitation," J. Pain 5, 2004, 392-405.
Su et al., "Lithium enhances the neuronal differentiation of neural progenitor cells in vitro and after transplantation into the avulsed ventral horn of adult rats through the secretion of brain-derived neurotrophic factor," J. Neurochem. 108, 2009, 1385-1398.
Takahashi et al., "Dermatomes in the rat limbs as determined by antidromic stimulation of sensory C-fibers in spinal nerves," Pain 67, 1996, 197-202.
Tan et al., "Neuropathic pain memory is maintained by Rac1-regulated dendritic spine remodeling after spinal cord injury," J. Neurosci. 28, 2008, 13173-13183.
Thompson et al., "Leukemia inhibitory factor induces mechanical allodynia but not thermal hyperalgesia in the juvenile rat," Neuroscience 71, 1996, 1091-1094.
Vierck Jr. et al., "Pain following spinal cord injury: animal models and mechanistic studies," Pain 89, 2000, 1-5.
Wieseler et al., "Below Level Central Pain Induced by Discrete Dorsal Spinal Cord Injury," Journal of Neurotrauma 27, Sep. 2010, 1697-1707.
Yezierski, "Pain following spinal cord injury: central mechanisms," Handb. Clin. Neurol. 81, 2006, 293-V.
Yezierski "Spinal Cord Injury: A Model of Central Neuropathic Pain," Neurosignals, 14, 4, Oct. 2005, 182-193.
Yezierski et al., "Excitotoxic spinal cord injury: behavioral and morphological characteristics of a central pain model," Pain 75, 1998, 141-155.
Yokota et al., "Sympathetic skin response in patients with multiple sclerosis compared with patients with spinal cord transection and normal controls," Brain 114, 1991, 1381-1394.
Zhao et al., "Extracellular signal-regulated kinase-regulated microglia-neuron signaling by prostaglandin E2 contributes to pain after spinal cord injury," J. Neurosci. 27, 2007, 2357-2368.
Zhou et al., "Differences in c-jun and nNOS expression levels in motoneurons following different kinds of axonal injury in adult rats," Brain Cell Biol. 36, 2008, 213-227.
PCT International Search Report and Written Opinion dated Oct. 6, 2009, PCT/US2009/053915, 25 pages.
Rodrigues-Filho, Avulsion injury of the rat brachial plexus triggers hyperalgesia and allodynia in the hindpaws: a new model for the study of neuropathic pain, *Brain Res.* (Aug. 29, 2003), 982(2):186-194.
Non-Final Office Action dated Mar. 4, 2013, U.S. Appl. No. 13/059,027, 10 pages.
Australian Office Action dated Apr. 16, 2012, Australian Patent Application No. 2009281824, 2 pages.
European Search Report dated Jan. 17, 2012, European Patent Application No. 098073778, 10 pages.
Felipe, et al., "Excitotoxic injury to the rat spinal cord does not promote sprouting of myelinated fibers to the superficial laminae," *Database Biosis [online] Biosciences Information Service*, Philadelphia, Pennsylvania, 2003, 3 pages.
Saade, et al., "The Role of the Dorsal Columns in Neuropathic Behavior: Evidence for Plasticity and Non-Specificity," Neuroscience, 2002, vol. 115, No. 2, pp. 403-413.
Scholz, et al., "Blocking Caspase Activity Prevents Transsynaptic Neuronal Apoptosis and the Loss of Inhibition in Lamina II of the Dorsal Horn after Peripheral Nerve Injury," *The Journal of Neuroscience*, Aug. 10, 2005, vol. 25, No. 32, pp. 7317-7323.
Ramer, et al., 2004, The Journal of Neuroscience, 24: 10796-10805.
Aoki, et al., 2003, Brain Research, 989: 214-220.

\* cited by examiner

FIG.7B

RODENT MODEL OF CENTRAL NEUROPATHIC PAIN CAUSED BY DORSAL ROOT ENTRY ZONE AVULSION AT T13

CROSS REFERENCE TO RELATED APPLICATION

This patent application is a continuation of U.S. patent application Ser. No. 12/541,754, now U.S. Pat. No. 8,502, 017, filed Aug. 14, 2009 and entitled "A Rodent Model of Central Neuropathic Pain," which claims benefit under 35 U.S.C. §119(e) to U.S. Provisional Patent Application No. 61/088,978, filed Aug. 14, 2008, and entitled "Animal Model of Central Neuropathic Pain and Methods of Making and Using the Same," both of which are incorporated herein by reference in their entirety.

FIELD

The disclosure relates to an animal model of central neuropathic pain, methods of making the same, and methods of using the same to screen for therapeutic agents useful in the treatment of central neuropathic pain, particularly that associated with spinal cord injury.

BACKGROUND

All vertebrate animals have a central axis of the body that consists of the spinal or vertebral column. The vertebral column consists of a number of connected irregular bones, termed the vertebrae, which surround and thereby protect a spinal cord. The vertebrae also support the weight of the trunk and transmit the weight to the lower limbs.

The vertebrae are grouped according to the region in which they lie—cervical, thoracic, lumbar, sacral and coccygeal or caudal. Each vertebra has a ventral and dorsal side. In series with each vertebra are a number of spinal nerves. Each nerve is formed by the union of an anterior (motor) and posterior (sensory) nerve-root. The posterior or dorsal nerve-roots are the central branches of the axons of the unipolar cells of the spinal ganglia. There are thirty-one pairs of spinal nerves in the human: 8 cervical, 12 thoracic, 5 lumbar, 5 sacral and 1 coccygeal.

Severe or disabling chronic pain is often observed after spinal cord injury (SCI). It is believed that these forms of pain have a central origin.

Current models of SCI are problematic in that they typically induce urinary retention, paresis/paralysis, and autotomy. Urinary retention and associated infections can be detrimental to the health of the animals, while motor dysfunction and autotomy make it very difficult if not impossible to cleanly assess for for exaggerated pain. Further, in deafferentation models to date, such as extradural posterior cervical rhizotomy (e.g., Lombard et al., Pain, 6:163-174, 1979), the only available indicator of pain is autotomy, owing to deafferentation of the territory of interest. Additionally, the hyperreflexia and spasticity observed in many models can further complicate the interpretation of experimental results.

There exists a need for valid animal models of central neuropathic pain, including below-level pain which is the most common and intractable neuropathic pain associated with SCI (Yezierski, Neurosignals, 14:182-193, 2005).

SUMMARY

The present inventor has solved the problems associated with previous neuropathic pain models by producing a model that provides for the study of exaggerated pain states using methods standard in the pain field in animals with uncompromised health and motor function. The model derives from the surprising finding that manipulation of DREZ fibers at particular spinal cord segments may be used to generate aberrant spinal cord activity and an increased pain response while preserving motor function and sensory capabilities in the affected territory. The present disclosure also provides a valid model of central neuropathic pain exhibiting below-level pain, the most common and intractable neuropathic pain observed in SCI. The preservation of sensation and motor control in the affected territory of the subject animal model facilitates the convenient assessment of pain and pain modulation under experimental conditions, and thereby provides a convenient tool for analyzing the therapeutic efficacy of candidate agents in the treatment of central neuropathic pain.

DREZ lesions have previously been performed in attempts to ameliorate existing pain in patients and in animal models of neuropathic pain. The inventors have made the surprising finding that DREZ manipulations, such as dorsal root avulsion or similar manipulations resulting in partial injury within the dorsal horn of the spinal cord, when performed in normal animals without pre-existing neuropathic pain, can generate an increased pain response in the subject animals while maintaining sensation and motor control in the affected territory.

The ease of generating the present animal model, and the health and resultant ease of maintaining the same make the present invention a model for screening candidate agents for efficacy in the treatment of central neuropathic pain. Unlike other SCI models, the subject model does not exhibit compromising characteristics such as spasticity, hyperreflexia, bladder infection, loss of motor function, or loss of sensation in the affected territory. Additionally, the DREZ manipulations undertaken may be unilateral, and may be limited to a single DREZ. These manipulations can produce an increased pain response in an affected territory which is more spatially discrete than that achieved in previous models. Further, the motor and sensory tracts of the spinal cord remain intact and motor and sensory function are largely preserved in the present model, except for the limited loss of sensation mediated by fibers of the manipulated DREZ(s).

Accordingly, in one aspect, the disclosure describes an animal model of central neuropathic pain.

In one embodiment, the disclosure describes a mammalian model of central neuropathic pain, wherein the mammal exhibits an increased pain response while maintaining sensation and motor control in the affected territory.

In another embodiment, the mammal comprises a partial injury of the dorsal horn at one or more spinal segments rostral to the level of the affected territory.

The subject model does not require a contusion injury or spinal cord transection, and the motor and sensory tracts of the spinal cord remain intact.

Examples of the increased pain response observed in the subject model include but are not limited to one or more of the following: increased response to radiant heat (Hargreaves test), mechanical allodynia (von Frey test), cold allodynia, and mechanical hyperalgesia.

In another embodiment, the subject model exhibits below-level pain. In certain embodiments, the DREZ fibers at and/or caudal to T3 and at and/or rostral to L1 are impaired. In another embodiment, the DREZ fibers at and/or caudal to T3 and at and/or rostral to L2 are impaired. In another embodiment, the DREZ fibers at and/or caudal to T3 and at and/or rostral to L3 are impaired. In certain embodiments, DREZ impairment is the result of DREZ avulsion.

In another embodiment, the subject model comprises a partial injury to the dorsal horn that is the result of DREZ avulsion at one or more spinal levels, or the result of a manipulation producing a comparable partial injury to the dorsal horn, wherein the animal lacks a spinal cord injury compromising motor or sensory tracts of the cord.

In one embodiment, DREZ fibers at more than one spinal segment are impaired. In one embodiment, DREZ fibers at consecutive spinal segments are impaired. In one embodiment, DREZ fibers are bilaterally impaired at one or more spinal segments.

In embodiment, aberrant activity is observed in the subject model in Rexed laminae 1-3.

In one embodiment, the subject model is a rodent and the DREZ fibers that are impaired include DREZ fibers at L1.

In one embodiment, the subject model is a rodent and the DREZ fibers that are impaired consist essentially of DREZ fibers at L1.

In one embodiment, the subject model is a rodent and the DREZ fibers that are impaired include DREZ fibers at T13 and L1.

In one embodiment, the subject model is a rodent and the DREZ fibers that are impaired consist essentially of DREZ fibers at T13 and L1.

In one embodiment, the subject model is a rodent and the affected territory includes the hindpaw but not the entire hindlimb.

In one embodiment, the subject model is a rodent and the affected territory includes the forepaw but not the entire forelimb.

In one embodiment, the subject model is a rodent and the affected territory is within the hindlimb, and the impaired DREZ fibers are rostral to L4.

In one aspect, the disclosure describes methods of generating an animal model of central neuropathic pain disclosed herein. The methods comprise inducing a partial injury of the dorsal horn without causing a spinal cord injury compromising motor or sensory tracts of the cord.

In certain embodiments, the partial injury is induced by DREZ avulsion. In another embodiment, the partial injury is induced by microcoagulation. In another embodiment, the partial injury is chemically induced. In another embodiment, the partial injury is photochemically induced. In another embodiment, other means of creating the required partial injury of the dorsal horn are used which may include mechanical lesions such as a knife cut or myelotomy, or inserting biological substances e.g., cells such as activated glia, which may release chemical substances such as inflammatory cytokines that may act on any of the cell types in the dorsal grey matter or dorsal root entry zone in a deleterious fashion.

In one aspect, the disclosure describes methods of screening candidate agents for bioactivity and potential therapeutic efficacy in the treatment of central neuropathic pain. The methods comprise administering a candidate agent to an model animal disclosed herein, detecting a reduction in altered pain response therein, and thereby determining the candidate agent has bioactivity and potential therapeutic efficacy.

In one aspect, the disclosure describes therapeutic agents obtained by screening methods disclosed herein.

BRIEF DESCRIPTION OF THE DRAWINGS

FIG. 1. Data showing results of DREZ avulsion at T13/L1 on the left side of rat. Testing for allodynia was done using the von Frey hair test, beginning day one post surgery and continuing daily over the subsequent four weeks. The results show reliable separation between sham and avulsion groups.

DETAILED DESCRIPTION

The following definitions are provided to facilitate the understanding of certain terms used frequently herein and are not meant to limit the scope of the present disclosure.

"Dorsal root entry zone" (DREZ) refers to the area of the dorsal grey matter of the spinal cord in the region of the dorsal roots for a particular region of the spinal cord. A large portion of these fibers terminate at the level of entry in the dorsal horn of the spinal cord. For purposes of the present disclosure, a DREZ includes any portion of the entry zone area from the dorsal surface of the spinal cord where the roots enter to a depth of at least Rexed lamina III in the dorsal horn. Also note that there is a right and left DREZ at each level of the spinal cord, and that unless specified, the term DREZ treats the right and left DREZ interchangeably. In addition, the electrical activity in the left and right DREZ at a particular level do not necessarily have to be symmetrical, i.e., one side may be manipulated and show aberrant neuroelectric activity and the other may show normal neuroelectric activity.

"At-level pain" refers to pain that is perceived to occur at the level of injury to the spinal cord. Note also that for purposes of the present disclosure, a level refers to a vertebra within the spine and its corresponding spinal cord level.

"Below-level pain" refers to pain that is perceived to occur at least one level below the site of injury to the spinal cord. In the animal model of the present disclosure, below-level pain refers to pain perceived below the level of DREZ manipulation.

Above-level pain refers to pain that is perceived to occur at least one level above the site of injury to the spinal cord. In the animal model of the present disclosure, above-level pain refers to pain perceived above the level of DREZ manipulation.

As used herein, "increased pain response" refers to an increased pain response to external stimuli. An increased pain response can include but is not limited to hyperalgesia and allodynia. The exaggerated pain state observed in the subject animal model includes an increased pain response.

As used herein, "affected territory" refers to tissue and structures exhibiting altered pain response as a result of the impairment of DREZ fibers.

As used herein, "maintaining sensation and motor control in the affected territory" refers to substantial maintenance of sensation and motor control in the affected territory. Sensation and motor control in the affected territory are maintained such that a response to an external stimulus may be elicited.

Animal Models of Neuropathic Pain

The focus of the present disclosure is the production of an animal model of central neuropathic pain. This may be accomplished by a variety of DREZ manipulation methods that effect a partial injury in the dorsal horn of the spinal cord at one or more levels, and preferably in a region of the dorsal horn corresponding to at least one of Rexed laminae I-III, though deeper layers may also be affected.

The model animals are non-human mammals that have an exaggerated pain state and exhibit increased pain responses. In certain embodiments, the disclosure describes a model of below-level pain, wherein an increased pain response may be elicited in a dermatome that maps to a spinal segment which is caudal to that at which the DREZ fiber manipulations of the disclosure are done.

Exemplary non-human mammals upon which the disclosure can be based include, but are not necessarily limited to, small laboratory animals, e.g., mice, rats, guinea pigs, hamsters, and large animal models, e.g., sheep, pigs, primates, and the like.

In one embodiment, the model animal is of the genus *Rodentia*, preferably a mouse or rat.

Included among the animals contemplated for use in the disclosure are transgenic animals. The present disclosure contemplates the use of such animals to analyze genetic effects on the generation, maintenance, and modulation of neuropathic pain. The animals contemplated for use include knock-out and knock-in animals.

The term "transgene" is used herein to describe genetic material which has been or is about to be artificially inserted into the genome of a mammalian cell.

By "transgenic animal" is meant a non-human animal, usually a mammal, having a non-endogenous (i.e., heterologous) nucleic acid sequence present as an extrachromosomal element in a portion of its cells or stably integrated into its DNA. In certain embodiments, heterologous nucleic acid is introduced into the germ line by genetic manipulation of, for example, embryos or embryonic stem cells of the host animal according to methods well known in the art. A "transgene" is meant to refer to such heterologous nucleic acid, e.g., heterologous nucleic acid in the form of an expression construct (e.g., for the production of a "knock-in" transgenic animal) or a heterologous nucleic acid that upon insertion within or adjacent to a target gene results in a decrease in target gene expression (e.g., for production of a "knock-out" transgenic animal).

A "knock-out" of a gene means an alteration in the sequence of the gene that results in a decrease of function of the target gene, preferably such that target gene expression is undetectable or insignificant. Transgenic knock-out animals can comprise a heterozygous knock-out of a target gene, or a homozygous knock-out of a target gene. "Knock-outs" as used herein also include conditional knock-outs, wherein alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration.

A "knock-in" of a target gene means an alteration in a host cell genome that results in altered expression (e.g., increased (including ectopic) or decreased expression) of a target gene, e.g., by introduction of an additional copy of the target gene, or by operatively inserting a regulatory sequence that provides for altered expression of an endogenous copy of the target gene. "Knock-in" transgenics can comprise a heterozygous knock-in of the target gene or a homozygous knock-in of a target gene. "Knock-ins" also encompass conditional knock-ins.

In one embodiment, the model animal is a transgenic mouse. In one embodiment, the transgenic mouse comprises a transgene that is capable of modulating a pain response. In one embodiment, the transgenic mouse is a knockout mouse, wherein a gene capable of modulating a pain response has been disrupted. Mice suitable for use in the present disclosure can be produced from any of a variety of background strains including, but not necessarily limited to, the strains C.B-17, C3H, BALB/c, C57131/6, AKR, BA, B10, 129, etc. The host animal may be either male or female.

Methods of Making Transgenic Animals

Any of the variety of means known in the art for making transgenic animals may be used.

DNA constructs for random integration need not include regions of homology to mediate recombination. Where homologous recombination is desired, the DNA constructs will comprise at least a portion of the target gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see for example Keown et al. (1990) Methods in Enzymology 185:527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are typically obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification may be mated to produce homozygous progeny. If the gene alterations cause lethality at some point in development, tissues or organs can be maintained as allogeneic or congenic grafts or transplants, or in in vitro culture.

Means for Generating Animal Model

Any of a variety of means may be used to generate the subject animal model. What is required is that the particular means used achieves the partial injury to the dorsal horn that is exemplified herein using DREZ avulsion. The partial injury is characterized by partial loss of nerve endings around secondary nerve cell bodies within the dorsal horn, and other changes described herein.

Figure 4A:
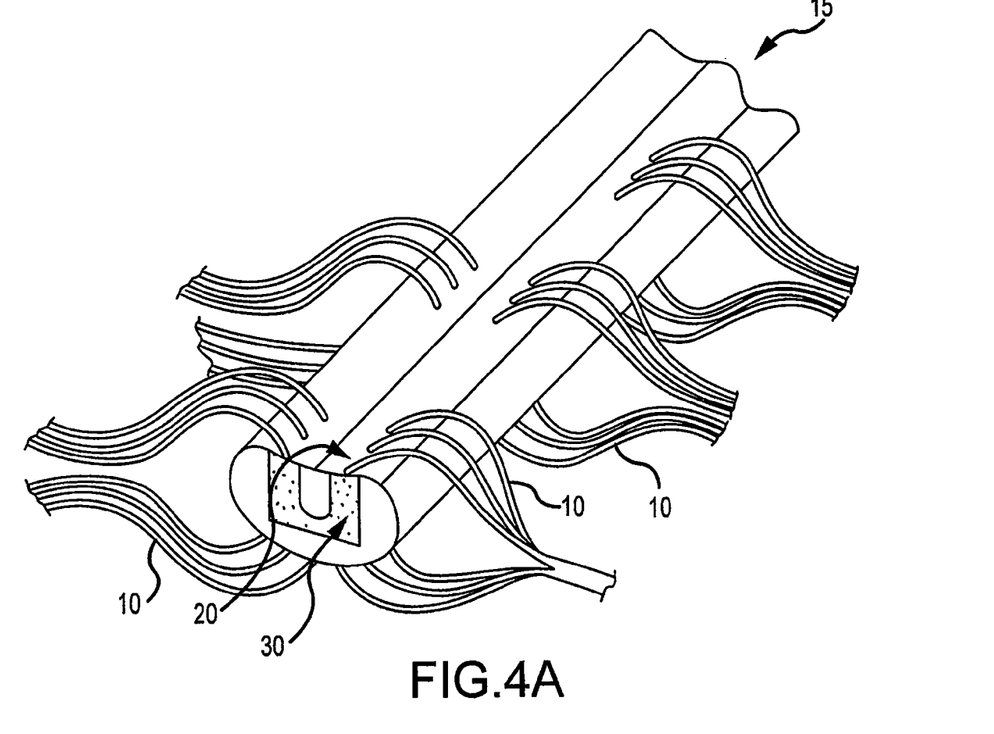
FIGS. 4A and 4B. Schematic of dorsal rootlet avulsion at L1.
Figure 4B:
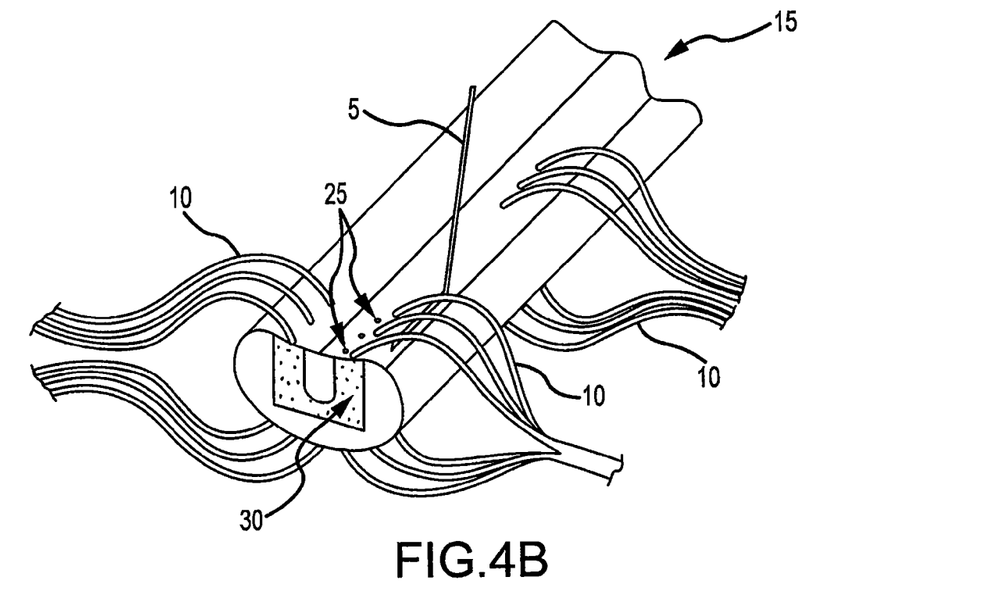

In certain embodiments, avulsion of one or more DREZs is done to generate the present animal model. "DREZ avulsion" refers to avulsing or pulling some or all of the sensory rootlets 10 out of one or more dorsal root entry zones 20. This can be done with any type of instrument 5 that can effectively be used for the intricate pulling out of the rootlets 10 (see FIGS. 4A and 4B).

In another embodiment, thermal means may be used to create a partial injury. For example, raidofrequency microcoagulation may be used, wherein temperatures of less that 85° C., more preferably less than 80° C., more preferably less than 75° C., more preferably less than 70° C. are used.

Other means of creating the required partial injury of the dorsal horn include chemical lesions, mechanical lesions such as a knife cut or myelotomy, or inserting biological substances, e.g., cells such as activated glia, which may release chemical substances such as inflammatory cytokines that may act on any of the cell types in the dorsal grey matter or dorsal root entry zone in a deleterious fashion.

The increased pain response exhibited by the subject animals is typically observed by two weeks post surgery and lasts for more than one month, preferably more than several months, preferably more than a year.

Selection of DREZ

It has been reported that the correlation between DREZs with spontaneous hyperactivity and perceived regions of pain in SCI subjects does not follow traditional dermatomal mapping (Falci et al., J. Neurosurg. (Spine 2), 97:193-200, 2002). Rather, there appears to be a correspondence in part between the spatial layout of sympathetic innervation, spinal segments of DREZ hyperactivity and regions of perceived pain. That is, the relationship between the location of sympathetic neurons within the intermediolateral cell columns of the spinal cord and their target territory roughly corresponds to the mapping of perceived regions of below-level pain to specific DREZs. Neuroanatomical dissection and clinical study have suggested that the sympathetic supply to 'end' organs of the lower extremities originates in caudal thoracic and cephalad lumbar spinal cord segments, to the head and neck, cephalad thoracic spinal cord segments, and to regions in between, by the intervening spinal cord segments. See Pick, The Autonomic Nervous System: Morphological, Comparative, Clinical and Surgical Aspects, Philadelphia: J. B. Lippincott, 1970; Yokota et al., Brain 114:1381-1394 (1991). Afferent sympathetic supply may follow the efferent supply. Browder, Am J Surg 18:100-102 (1932); Echlin, J Neurosurg 530-533 (1949); Harris, Brit Med J 2:112-115 (1936); Pick, The Autonomic Nervous System Morphological, Comparative, Clinical and Surgical Aspects, Philadelphia: J. B. Lippincott, 1970; Shields, J Clin Neurophysiol 10:2-13 (1993). Using data provided by the illustrative somatotopic map, it is believed that pain occurring distal from an injury site (below-level pain) is mediated significantly by the sympathetic nervous system. It is also believed that anatomic regions of perceived pain are somatotopically mapped to specific DREZ segments of the spinal cord. Specifically, lumbar segments (L1 in particular) mediate pain from the feet, T11 and T12 segments, the leg, and T8-T10 segments, the gluteal, rectal and perirectal regions. More cephalad segments would mediate pain in the truncal region. It is also believed that cephalad segments could mediate pain subtended by those in more caudal segments by way of the sympathetic chain or interneuronal pathways.

For more teaching on the somatotopic map of specific DREZs to perceived regions of pain, see Falci et al., J. Neurosurg. Spine 2), 97:193-200, 2002, expressly incorporated herein in is entirety by reference. Further regarding the somatotopic map for neuropathic pain, see US 2007/0016264, which is expressly incorporated herein in its entirety by reference.

Accordingly, in the present disclosure, this non-traditional somatotopic map for pain sensation, which largely mirrors the layout of the sympathetic nervous system, may be used to determine which DREZ fibers should be impaired in order to achieve altered pain sensation in the desired territory of a model animal. For example, in certain embodiments, in order to produce hindpaw pain in a rat, DREZs at L1, more preferably levels T13-L1, are manipulated to partially injure the dorsal horn.

Above level pain is also contemplated. For example, the internediolateral cell columns at T1 and T2 serve the upper extremities, neck and head. DREZ avulsion at T1 or T2, or partial injury by other means, is contemplated for the production of an animal model exhibiting above-level pain.

Screening Assays

The subject animal model can be used in a variety of screening assays to identify agents that are useful in the treatment of central neuropathic pain. In one embodiment, one or more model animals of the disclosure may be used to screen agents for their ability to inhibit the altered pain response observed. In another embodiment, one or more model animals of the disclosure can be used to screen agents for their ability to reversing glial cell activation. The reversal of glial cell activation corresponds to reduction of below level pain in one or more animals.

The screening assays described herein include the testing of established pain treatments in this new experimental paradigm. These are included as candidate agents. "Candidate agents" is meant to include synthetic, naturally occurring, or recombinantly produced molecules (e.g., small molecule; drugs; peptides; antibodies (including antigen-binding antibody fragments) or other immunotherapeutic agents; endogenous factors present in eukaryotic or prokaryotic cells (e.g., polypeptides, plant extracts, and the like)); etc.). Of particular interest are screening assays for agents that have a low toxicity for human cells.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. A number of chemical libraries are known in the art and are contemplated for use in the disclosure.

In one embodiment, the subject animal model is used to identify agents that reduce an altered pain response.

Typically, the candidate agent is administered to the subject animal and the effects of the candidate agent are assessed relative to a control. In general, a detectable and significant decrease in the pain response of the subject animal following treatment with a candidate agent relative to control is indicative of therapeutic activity of the agent.

The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired effect is to be achieved, e.g., the CNS or the affected territory), orally, or by any other desirable means. Normally, the in vivo screen will involve a number of animals receiving varying amounts and concentrations of the candidate agent (from no agent to an amount of agent that approaches an upper limit of the amount that can be delivered successfully to the animal), and may include delivery of the agent in different formulations and routes. Moreover, the agents may be administered to the animals at various time points. The agents can be administered singly or can be combined in combinations of two or more, especially where administration of a combination of agents may result in a synergistic effect.

The activity of the candidate agent can be assessed in a variety of ways. For example, the effect of the agent can be assessed behaviorally, by examining, for example, the effect of the agent on the subject animals' increased response to radiant heat (Hargreaves test), mechanical allodynia (von Frey test), cold allodynia, and mechanical hyperalgesia.

Additionally, molecular and cellular assays may be undertaken to assess the activity of a candidate agent. For example, assays for activated glia, inflammatory cytokines, receptor upregulation or downregulation, etc. may be used. A number of such parameters are altered in the subject model, and the effect of candidate agent on the same may be detected and used as an output to determine bioactivity of the candidate agent.

In vitro assays are also contemplated. In one embodiment, cells from the subject animals are cultured and the activity of a candidate agent is tested in vitro.

Therapeutic Agents

In one aspect, the disclosure describes compositions that have been determined to have the ability to modulate an increased pain response using the subject animal model. These may be used as therapeutic agents.

The term "therapeutic agent" as used herein refers to any molecule, e.g., protein or small molecule, pharmaceutical compound, antibody, antisense molecule, ribozyme, and the like, useful in the treatment of a disease or condition.

The therapeutic agents may be administered in a physiologically acceptable carrier to a host for the treatment of pain. The therapeutic agents may be administered in a variety of ways, including orally, topically, parenterally e.g. subcutaneously, intraperitoneally, intravascularly, by inhalation, intrathecally, etc. Depending upon the manner of introduction, the compounds may be formulated in a variety of ways. The concentration of therapeutically active compound in the formulation may vary from about 0.1-100 wt. %.

The pharmaceutical compositions can be prepared in various forms, such as granules, tablets, pills, suppositories, capsules, suspensions, salves, lotions, and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The terms "treatment", "treating" and the like are used herein to generally mean obtaining a desired pharmacologic and/or physiologic effect.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000).

The pharmaceutical compositions of the disclosure include a "therapeutically effective amount". A "therapeutically effective amount" refers to an amount effective, at dosages and for periods of time necessary, to achieve the desired therapeutic result. A therapeutically effective amount may vary according to factors such as the disease state, age, sex, and weight of the individual. A therapeutically effective amount is also one in which any toxic or detrimental effects are outweighed by the therapeutically beneficial effects.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions.

EXPERIMENTAL

Example 1

Production of Animal Model of Neuropathic Pain

Rats were anesthetized using isoflurane. Under aseptic condition, the skin was incised in the midline along the posterior thoracolumbar region. The paravertebral muscles were retracted laterally to expose the posterior aspect of the spinal laminae. Laminectomies were performed and the dura mater then incised along the midline to expose the dorsal rootlets 10 of T13 and L1. The dorsal rootlets of T13 and L1 were then avulsed out of the spinal cord 15 on the left side using microstrumentation 5 (see FIG. 4B). A visual defect 25 in pia and dorsal cord where the rootlets 10 were avulsed can be seen in FIG. 4B. The grey matter 30 of the spinal cord 15 is also shown. Hemostasis was obtained and a layer of gelfoam placed over the dura. The wound was closed in layers. Perioperative antibiotics were administered in prophylaxis against infection.

Allodynia in Animal Model

Subject rats were tested for allodynia of the hindpaws with the von Frey hair test, beginning day one post surgery and continuing daily over the subsequent four weeks.

Figure 1:
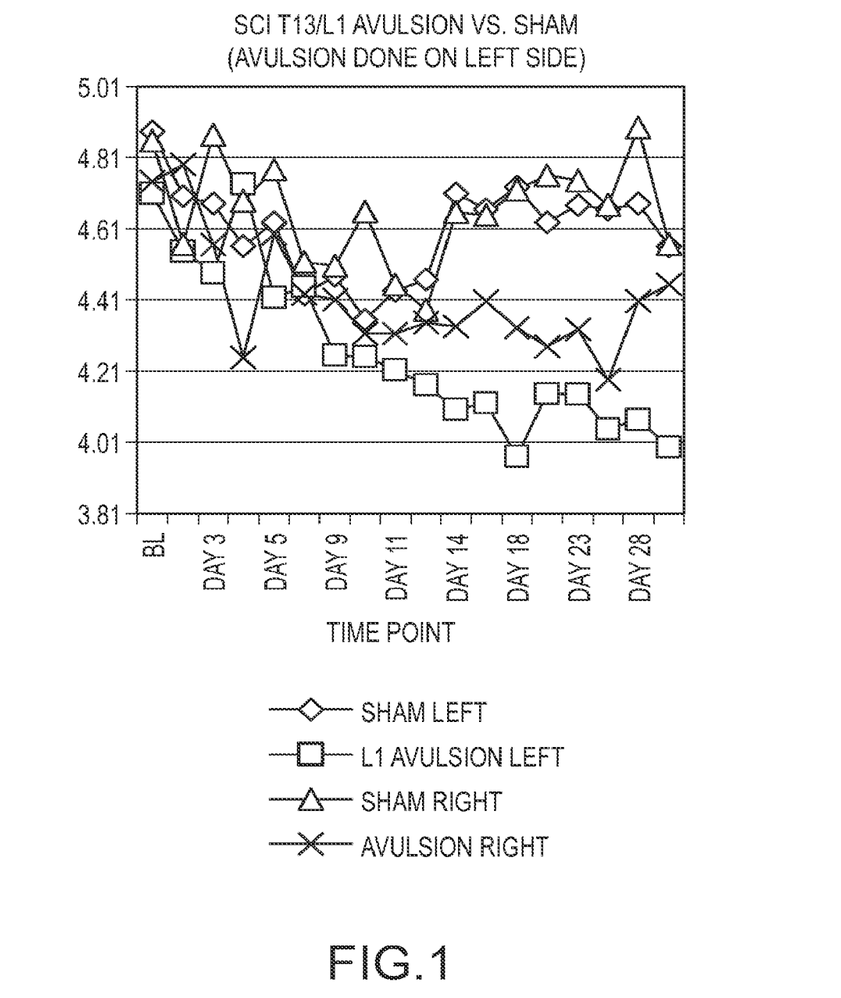

We characterized the time course of pain changes and patterns of dorsal root ganglia (DRG) & spinal glial activation following rapid avulsion of low thoracic/high lumbar dorsal roots at the dorsal root entry zone (DREZ). T13/L1 DREZ avulsion produces mechanical allodynia in the hindpaws (von Frey test) after a temporal delay, without compromising hindleg motor function. See FIG. 1.

Initially a comparison was made of avulsing a varying number of dorsal roots between T13 and L3 vs. sham controls. Animals were behaviorally tested prior to surgery and again at 3, 7, 14, 21, and 28 days post surgery. Mechanical allodynia was reliably seen beginning 7 days post surgery, and lasted for at least 28 days. Based on this, new groups of rats with unilateral T13/L1 DREZ avulsions or sham surgery were behaviorally tested as above, followed by brain, spinal cord and DRG collection at either 7, 14, 12 or 28 days. T13/L1 DREZ avulsions again induced reliable hindpaw allodynia compared to controls. The hindpaw allodynia was seen bilaterally; however, the effect was greater on the ipsilateral side compared to the contralateral side. The tissues are processed to define the pattern and rostrocaudal extent of glial activation across time resulting from T13/L1 DREZ avulsion vs. sham surgery, and changes in the expression of various factors.

Example 2

Administration of Agent Reduces Allodynia in Model

Figure 2:
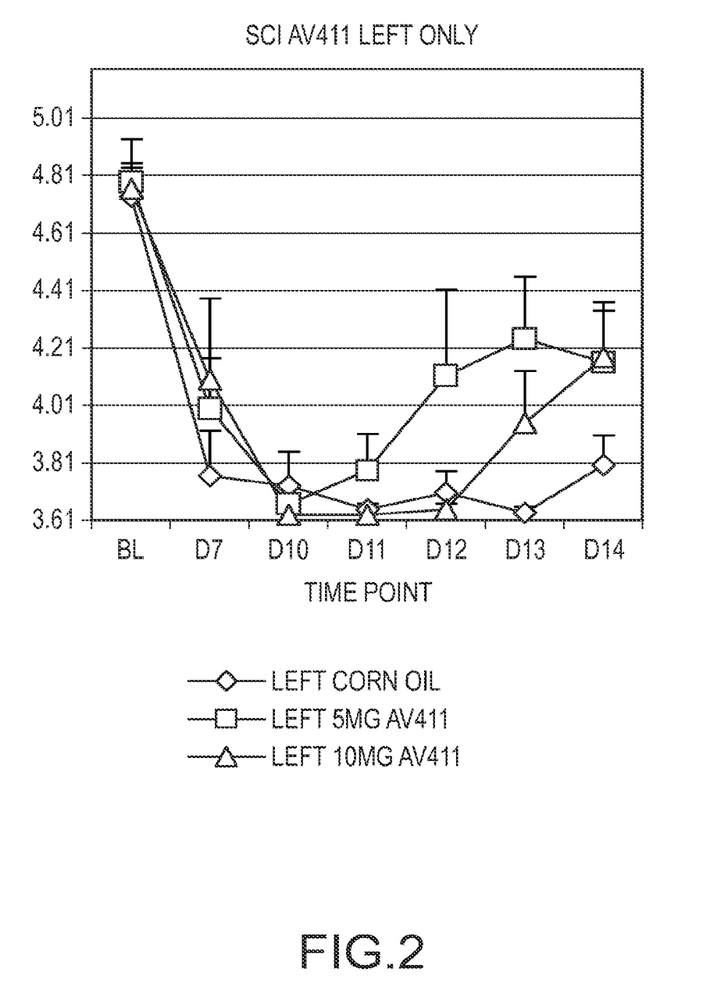
FIGS. 2 and 3. Data showing the effect of the drug ibudilast (also known as AV411, or 2-methyl-1-(2-propan-2-ylpyrazolo[1,5-a]pyridin-3-yl)propan-1-one) on allodynia in rats having DREZs avulsed at T13/L1.
Figure 3:
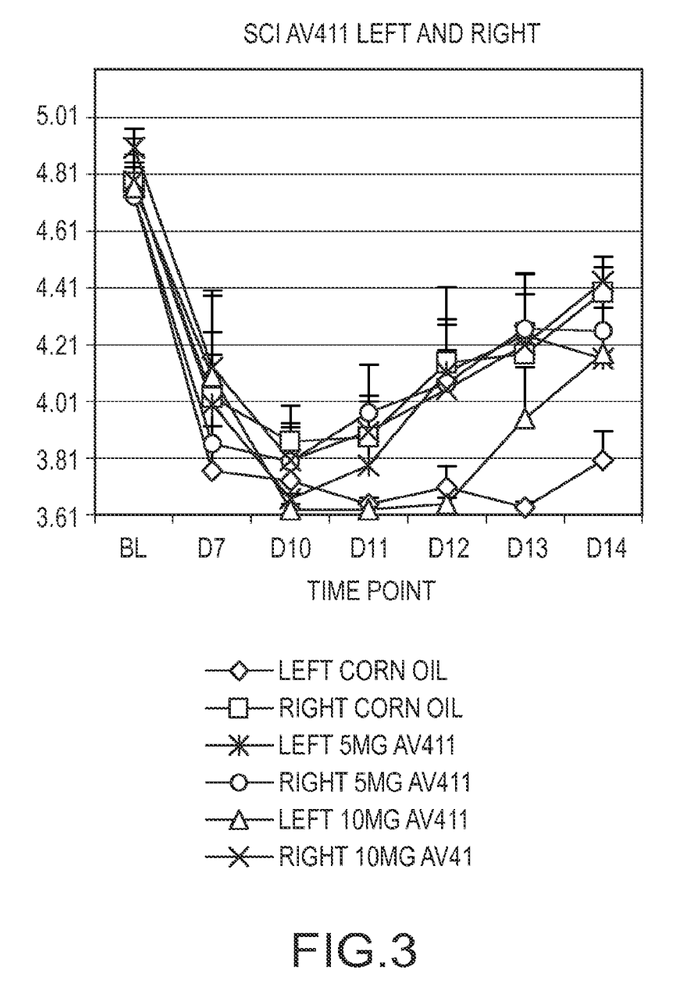

Rat animal model was generated similar to above. In one experiment, DREZ avulsion was unilateral (FIG. 2). In one experiment, DREZ avulsion was bilateral (FIG. 3). Ibudilast was delivered intrathecally daily in a corn oil carrier, with sham controls receiving only the corn oil. Ibudilast decreases allodynia in the model.

Example 3

The dorsal spinal cord was exposed by laminectomy at the T13/L1 spinal level. The T13 and L1 dorsal roots were each isolated, clamped at the dorsal root entry zone (DREZ) and briskly pulled out of the spinal cord as described above.

Response thresholds on the von Frey test were recorded prior to and across a timecourse after either avulsion or sham surgery. Spinal cord tissues were collected 7, 14, 21, and 30 days post-surgery (n=5 avulsion and 1 sham at each timepoint). After overdosing with sodium pentobarbital, rats were transcardially perfused with physiological saline followed by 4% paraformaldehyde. Spinal cords were post-fixed in 4% paraformaldehyde for 15 minutes and then transferred to 30% sucrose. The spinal cords were blocked into 5-mm sections, one section including the site of injury and another 10-mm caudal to the site of injury. This latter site corresponds to L5/L6 which is the spinal site from which allodynia behaviors were elicited. These tissues were cryostat sectioned (20-um) and reacted by immunohistochemistry (ABC method) for expression of CD11b/c (microglial activation marker, OX42) and glial fibrillary acidic protein (astrocyte activation marker, GFAP).

Figure 5A:
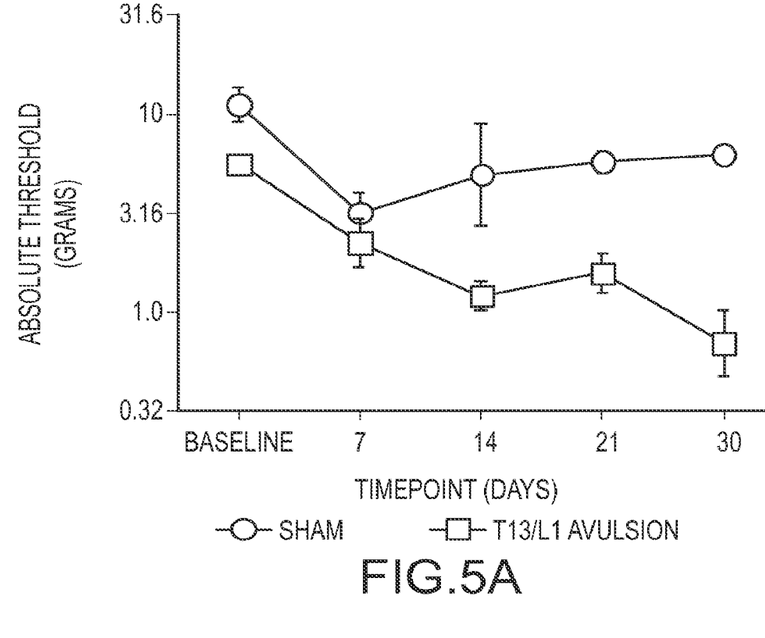
FIGS. 5A and 5B. Data showing unilateral T13/L1 avulsion produces sustained mechanical allodynia and may activate glia.
Figure 5B:
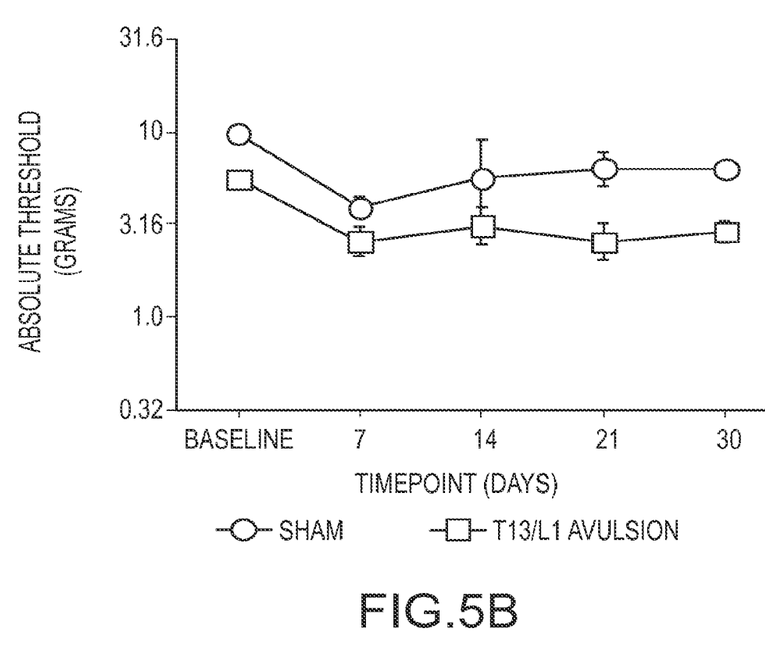

FIGS. 5A and 5B show unilateral T13/L1 avulsion produces sustained mechanical allodynia and may activate glia. Unilateral T13/L1 Avulsion induced reliable mechanical allodynia by day 14. Ipsilateral allodynia was maintained through the remainder of the 30 day timecourse. Mild contralateral allodynia was reliably observed on day 21, and remained through the end of the experiment. We are currently processing spinal cord tissue for immunohistochemistry in order to assess changes in glial activation.

Figure 6:
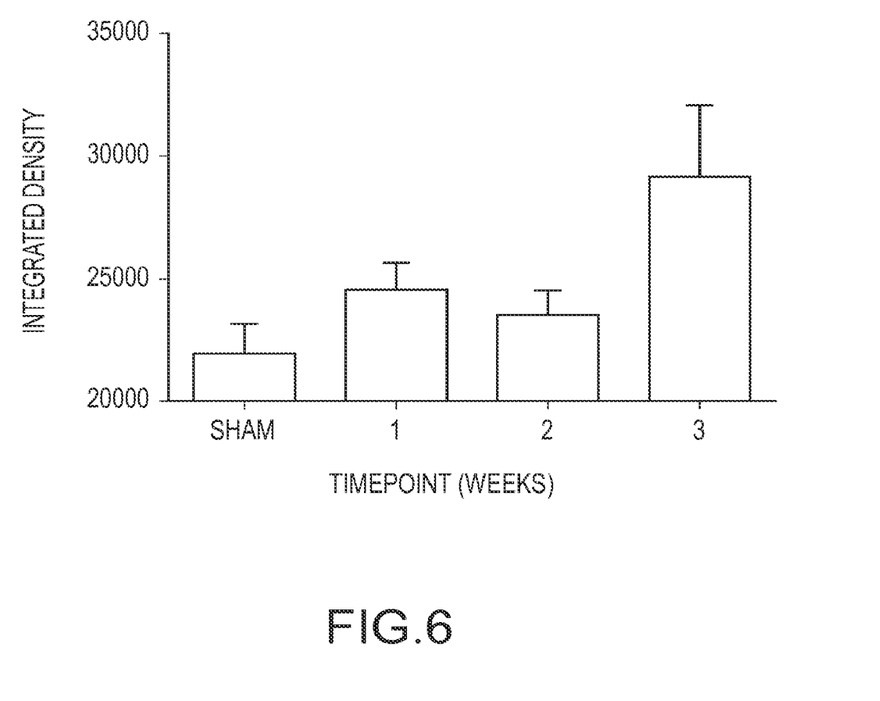
FIG. 6. Data showing increase in immunoreactivity for GFAP (an astrocyte activation marker) over 3 weeks.
Figure 7A:
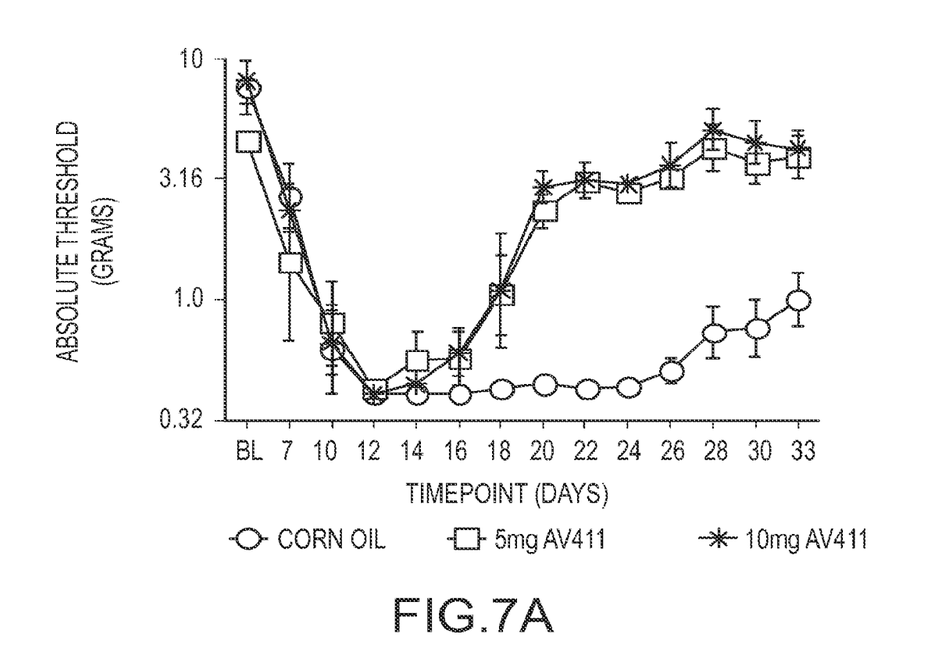
FIGS. 7A and 7B. Data showing that the glial modulator AV411 reverses bilateral allodynia induced by unilateral T13/L1 dorsal root avulsion.
Figure 7B:
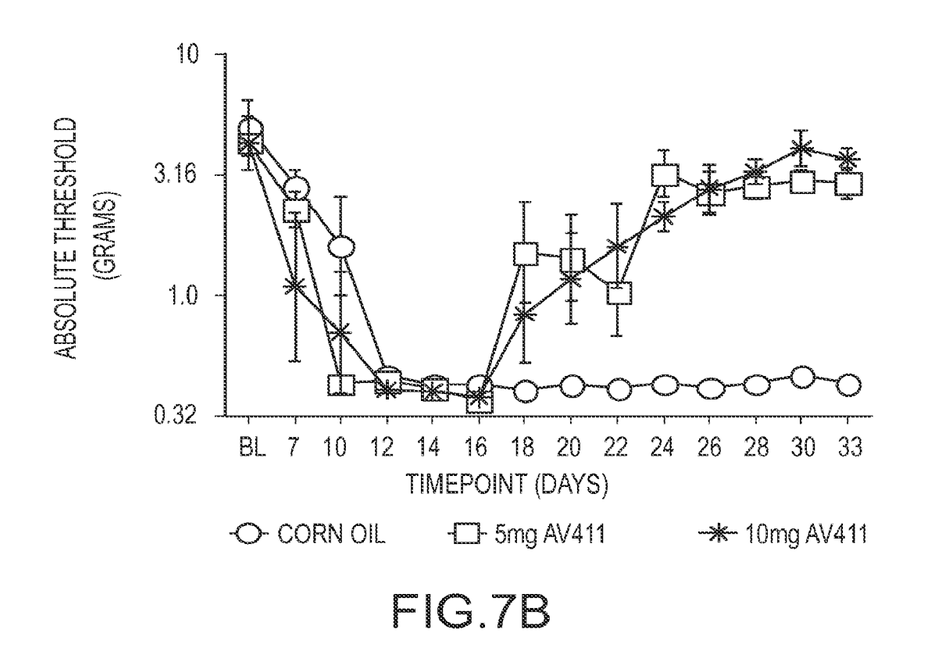

As depicted in FIG. 6, an increase in immunoreactivity for GFAP astrocyte activation marker over 3 weeks was observed.

Example 4

Response thresholds on the von Frey test were recorded prior to and across a timecourse through 42 days after either avulsion, rhizotomy, or sham surgery (n=2 for sham and avulsion, n=4 for rhizotomy). unilateral T13/L1 avulsion produces sustained mechanical allodynia beyond that induced by rhizotomy. Allodynia was reliably observed 14 days after avulsion and rhizotomy procedures, compared to sham controls. Rats that received avulsion surgery had absolute thresholds consistently below 1 gram whereas rats that received rhizotomy surgery had absolute thresholds consistently above 1 gram. Avulsion rats were still sensitive 42 days post-surgery while rhizotomy rats were close to their baseline levels.

Example 5

Injury at the T13 and L1 dorsal root entry zones results in exaggerated pain in the hind paws, which are innervated primarily by L5 and L6. Pain below the level of injury was demonstrated.

AV411 was administered to animals avulsed at the T13 and L1 dorsal root entry zones. The compound AV411 was administered to animals subject to the T13 and L1 hind paws. AV411 reversed allodynia induced by avulsion. The reversal begins after 5-6 injections and continues to reverse behavior until day 33. The contralateral paw began to resolve at day 28 and the ipsilateral paw was still sensitive at day 33. There were not differences between the 5 mg and 10 mg dose of AV411.

Response thresholds on the von Frey test were recorded prior to and across a timecourse after avulsion surgery. Beginning on Day 12 post-surgery, rats (n=4/group) received once daily s.c. injections of either the glial activation inhibitor AV411/Ibudilast (Sigma; 5-mg/kg or 10-mg/kg) or equivolume vehicle (corn oil; 0.5-ml/kg). Daily drug treatment and intermittent behavioral testing continued through 33 days after surgery.

Unilateral T13/L1 dorsal root avulsion was used to model exaggerated pain associated with spinal cord injury. T13 and L1 dorsal rootlets were avulsed. Administering AV411 induces bilateral mechanical allodynia in the hind paws lasting upwards of 1.5 months. This robust allodynia is sustained beyond that induced by rhizotomy.

Consistent with peripheral nerve injury models and other spinal cord injury models, avulsion surgery activates glia. Classically, astrocytes gradually become activated and sustain that level of activation over time, thereby maintaining the exaggerated pain state. Astrocyte activation appears to follow this pattern in our avulsion model.

The glial modulator AV411 reverses bilateral allodynia induced by unilateral T13/L1 dorsal root avulsion. Daily administration of AV411 reversed allodynia induced by avulsion. The reversal begins after 5-6 injections and continues to reverse behavior until day 33. The contralateral paw began to resolve at day 28 and the ipsilateral paw was still sensitive at day 33. There were not differences between the 5 mg and 10 mg dose of AV411.

All citations are expressly incorporated herein in their entirety by reference.

I claim:

1. A rodent model of central neuropathic pain, the rodent comprising a partial injury to the dorsal horn that is the result of dorsal root entry zone (DREZ) avulsion at T13, wherein the rodent exhibits an increased pain response while maintaining sensation and motor control in the affected territory, wherein the rodent lacks a spinal cord injury compromising motor or sensory tracts of the spinal cord, and wherein the rodent exhibits below-level pain.

2. A rodent model of central neuropathic pain, comprising a rodent that exhibits below-level pain comprising an increased pain response to stimulation of a target, wherein the rodent comprises a partial injury of the dorsal horn that is the result of dorsal root entry zone (DREZ) avulsion at T13, wherein said rodent exhibits aberrant activity of the spinal cord at a level rostral to the level at which the majority of sensory neurons serving the target enter the spinal cord, and wherein the rodent lacks a spinal cord injury compromising motor or sensory tracts of the spinal cord.

3. A rodent model of below-level pain, the rodent comprising a partial injury of the dorsal horn that is the result of dorsal root entry zone (DREZ) avulsion at T13, and exhibits below-level pain comprising an increased pain response.

4. The rodent model according to claim 1, wherein DREZ fibers are bilaterally avulsed at one or more spinal segments.

5. The rodent model according to claim 1, wherein the DREZ fibers that are avulsed include DREZ fibers at T13.

6. The rodent model according to claim 1, wherein the DREZ fibers that are avulsed consist essentially of DREZ fibers at T13.

7. The rodent model according to claim 2, wherein aberrant activity is observed in Rexed laminae 1-3.

8. The rodent model according to claim 1, wherein the affected territory includes the hindpaw but not the entire hindlimb.

9. The rodent model according to claim 1, wherein the affected territory is within the hindlimb.

10. The rodent model of claim 2, wherein the affected territory includes the hind paw but not the entire hind limb or is within the hind limb.

11. The rodent model of claim 3, wherein the affected territory includes one of the hind paw but not the entire hind limb or is within the hind limb.

* * * * *